United States Patent [19]

Haber

[11] Patent Number: 5,356,384

[45] Date of Patent: Oct. 18, 1994

[54] SYRINGE WITH NEEDLE RECAPPING SYSTEM

[76] Inventor: John P. Haber, 4229 Byron, Houston, Tex. 77005

[21] Appl. No.: 12,331

[22] Filed: Feb. 2, 1993

[51] Int. Cl.$^5$ ............................................. A61M 5/00
[52] U.S. Cl. ................................. 604/110; 206/366; 128/DIG. 26; 211/71; 604/192
[58] Field of Search .............. 604/110, 192, 203, 403; 128/DIG. 26, 919; 206/366, 370, 438; 211/71, 74

[56] References Cited

U.S. PATENT DOCUMENTS

| | | | |
|---|---|---|---|
| 4,142,633 | 3/1979 | Raghavachari et al. | 206/366 |
| 4,383,615 | 5/1983 | Aquino | 211/60 R |
| 4,461,387 | 7/1984 | Belokin, Jr. | 211/71 |
| 4,596,562 | 6/1986 | Vernon | 604/192 |
| 4,717,386 | 1/1988 | Simmons | 604/192 |
| 4,742,910 | 5/1988 | Staebler | 206/365 |
| 4,763,867 | 8/1988 | Hungerford, Jr. | 248/544 |
| 4,767,012 | 8/1988 | Simmons | 211/89 |
| 4,802,579 | 2/1989 | Hall et al. | 206/366 |
| 4,844,249 | 7/1989 | Coulombe | 206/438 |
| 4,846,803 | 7/1989 | Emerson | 604/263 |
| 4,852,814 | 8/1989 | Villaveces | 248/314 |
| 4,890,734 | 1/1990 | Gach | 206/366 |
| 4,903,832 | 2/1990 | Stewart | 206/366 |
| 4,906,235 | 3/1990 | Roberts | 604/192 |
| 4,915,225 | 4/1990 | Tabor, Jr. et al. | 206/368 |
| 4,915,698 | 4/1990 | Levenson | 604/192 |
| 4,921,199 | 5/1990 | Villaveces | 248/314 |
| 4,928,824 | 5/1990 | Barasch | 206/365 |
| 4,936,469 | 6/1990 | Drower | 211/69.8 |
| 4,938,354 | 7/1990 | Hernandez | 206/365 |
| 4,938,514 | 7/1990 | D'Addezio | 294/16 |
| 4,955,477 | 9/1990 | Bruno | 206/366 |
| 4,955,865 | 9/1990 | Steiner et al. | 604/192 |
| 4,973,315 | 11/1990 | Sincock | 604/192 |
| 4,979,945 | 12/1990 | Wade et al. | 604/192 |
| 4,981,476 | 1/1991 | Aichlmayr et al. | 604/192 |
| 4,986,816 | 1/1991 | Steiner et al. | 604/192 |
| 4,986,817 | 1/1991 | Code | 604/192 |
| 5,000,742 | 3/1991 | Morrison | 604/192 |
| 5,013,299 | 5/1991 | Clark | 604/114 |
| 5,024,666 | 6/1991 | Pituch | 604/263 |
| 5,037,400 | 8/1991 | Curry | 604/192 |
| 5,046,612 | 9/1991 | Mostarda et al. | 206/365 |
| 5,047,019 | 9/1991 | Sincock | 604/192 |
| 5,057,656 | 10/1991 | Galber | 206/366 |
| 5,067,532 | 11/1991 | Lang et al. | 141/329 |
| 5,078,695 | 1/1992 | Farrar, Jr. et al. | 604/192 |
| 5,078,696 | 1/1992 | Nedbaluk | 604/192 |
| 5,084,030 | 1/1992 | Byrne et al. | 604/198 |
| 5,086,922 | 2/1992 | Sagstetter et al. | 206/366 |
| 5,087,249 | 2/1992 | Deal | 604/192 |
| 5,092,462 | 3/1992 | Sagstetter et al. | 206/366 |
| 5,115,921 | 5/1992 | Lavelle | 211/71 |
| 5,128,105 | 7/1992 | Berthold et al. | 422/104 |
| 5,129,886 | 7/1992 | Sincock | 604/192 |
| 5,137,151 | 8/1992 | Choate | 206/370 |
| 5,143,414 | 9/1992 | Rosellini | 294/99.2 |
| 5,147,325 | 9/1992 | Mitchell et al. | 604/192 |
| 5,156,426 | 10/1992 | Graves | 294/1.1 |
| 5,160,324 | 11/1992 | Halbach | 604/192 |
| 5,171,224 | 12/1992 | Tucker | 604/110 |
| 5,183,469 | 2/1993 | Capaccio | 604/192 |
| 5,190,169 | 3/1993 | Sincock | 211/60.1 |

Primary Examiner—C. Fred Rosenbaum
Assistant Examiner—Chalin Smith
Attorney, Agent, or Firm—Pravel, Hewitt, Kimball & Krieger

[57] ABSTRACT

A recapping apparatus includes a generally U-shaped frame member having a plurality of spring biased attachment clips for receiving a syringe with needle cap so that the medical professional can remove the needle with syringe from the cap with one hand and thereafter replace the syringe with needle back into the cap in case it is needed for reuse. At the end of the period of use such as an operation, the syringes with needles inserted into the caps can be removed from the attachment clips and disposed of in a sharps container.

8 Claims, 2 Drawing Sheets

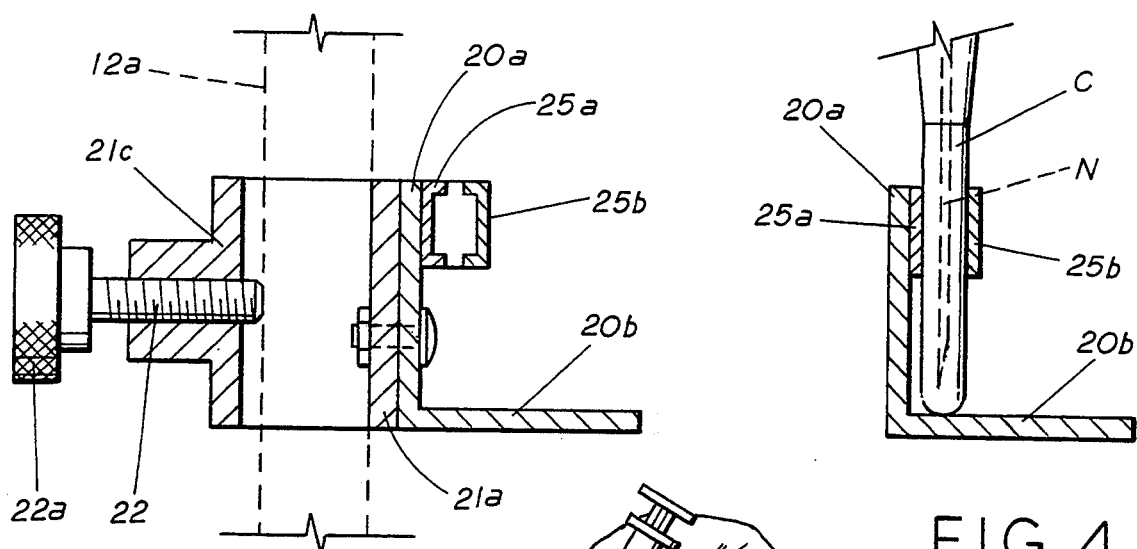
FIG. 3
FIG. 4
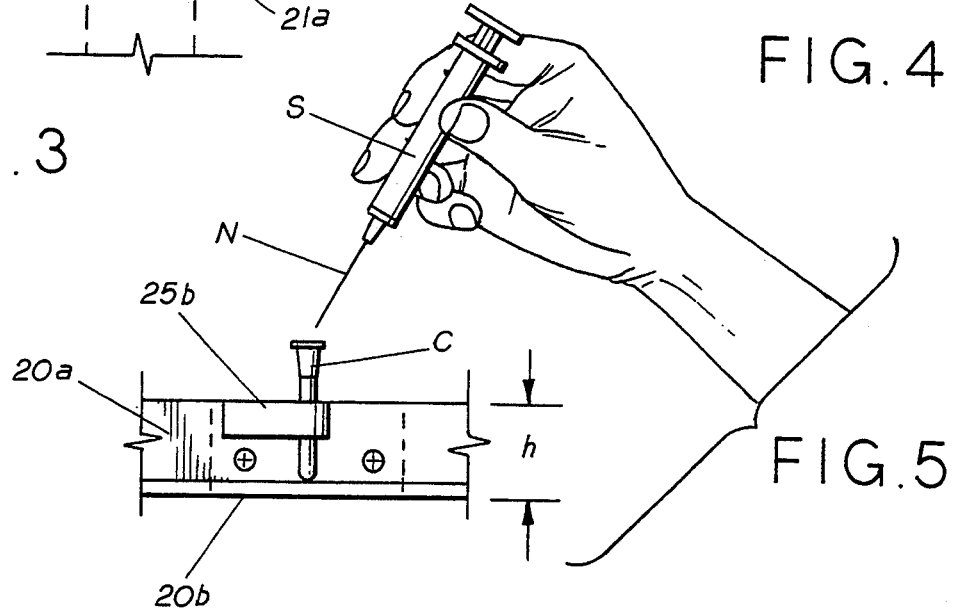
FIG. 5
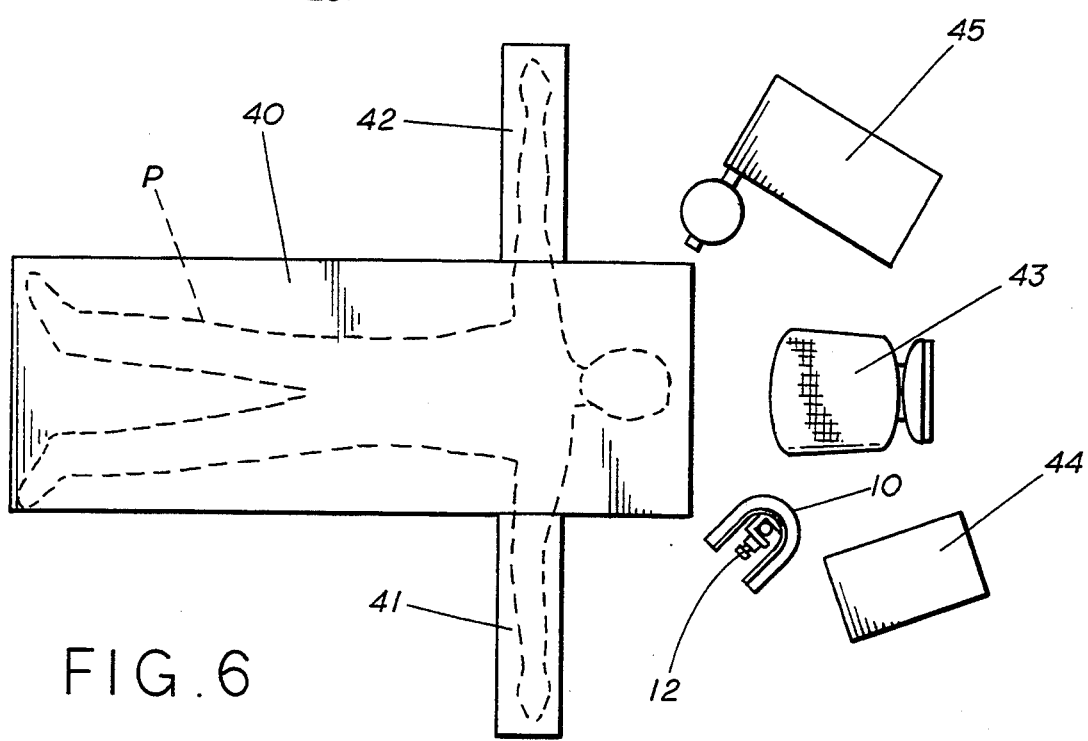
FIG. 6

SYRINGE WITH NEEDLE RECAPPING SYSTEM

SPECIFICATION

1. Field of the Invention

The field of this invention relates to a system for uncapping and recapping syringes with needles while eliminating the danger of needle sticks.

2. Background of the Invention

The danger of infection by the transfer of pathogens from a patient to a doctor or other medical professional, is at perhaps its greatest level due to the ever increasing presence of AIDS viruses. Of course, the presence of AIDS is not limited to patients, and AIDS may also be transferred from doctors or other medical professionals to the patients. One of the greatest dangers to the medical community is the needle "stick," where the medical professional accidentally punctures himself or herself with a needle which may have been exposed to the blood of a diseased patient. Such needle sticks are difficult to avoid in typical needle with syringe usage because the medical professional must expose the needle with syringe for usage and must then use it. Further, the medical professional must then dispose of the needle with syringe. And in the interim, it may be necessary for the medical professional to leave the needle with syringe on a table or other convenient location so that the needle with syringe may be used again. For example, it is not unusual for an anesthesiologist or nurse anesthetist during the course of a surgery to have several already used needles with syringes lying on a table, however, in spite of regulations against recapping with two hands, it is the general practice that the needles with syringes are recapped anyway.

Recapping of needles has become such a likely area for needles sticks that OSHA has promulgated regulations which actually prevent the medical professional from using two hands to replace a needle cap onto a needle with syringe.

Insofar as known to the inventor, there has been no successful remedy for this problem. Following the OSHA regulations is not a complete answer, for the medical professional is unable to recap the needle on a temporary basis and thus must leave the needles with syringes lying exposed if they are to be reused since they cannot be recapped. U.S. Pat. No. 4,985,020 of Kasuya discloses a needle cap having a guide portion to guide the needle into the cavity and a radially extending gripping tab so that the user may hold the cap by the gripping tab out of the line of reentry of the needle into the cap. Following the teaching of Kasuya, the medical professional must still hold the cap during re-insertion and thus, while there may be some reduction of exposure, the thumb and forefinger holding the cap are certainly still exposed to the potential of a needle stick. Sage Products, Inc. are currently marketing a product known as the "IV Pole Needle Resheather." The Sage needle resheather may be mounted on an "IV" pole and includes a series of conically shaped openings. The conically shaped openings are of various sizes for receiving needle caps of various sizes, which may be inserted into the appropriately sized hole and pushed down to be held in place so that the syringe with needle may be removed from the cap and then later resheathed. The advantage of such a system is that only one hand is required so that the OSHA regulation is not violated. The disadvantage of the system is that the cap must be inserted into the opening and frictionally held. Thus, it is up to the medical operator to properly fit the needle cap into the opening. If the needle cap is not fitted tightly, then the cap may become loose during removal of the syringe with needle, thus defeating the purpose and requiring the medical professional to use two hands to free the needle with syringe from the cap. It is therefore believed that there yet remains a need for a safe and reliable system for uncapping and recapping needles.

SUMMARY OF THE INVENTION

The apparatus of this invention is a needle recapping system which provides for reliable one-handed removal and replacement of a syringe with needle with no need for the second hand to be anywhere in the area. The apparatus of this invention includes a frame which may be attached to a stationary object such as an IV pole. The frame includes a plurality of spaced gripping mechanisms which are attached to the frame. Each gripping mechanism includes resiliently urged internal gripping surfaces to receive and hold a syringe with needle having a needle cap thereon. The syringe with needle is thereafter removable from the needle cap with the needle cap being held by the internal gripping surfaces. The syringe with needle may be easily re-inserted into the needle cap for temporary storage or for disposal. Each gripping mechanism includes a first gripping member attached to the frame and a second gripping member mounted for pivotal movement with respect to the first gripping member. A resilient element engages both the first and second gripping members to urge said members toward each other to resiliently grip the needle cap.

The features just described are only some of the features of this invention, which are further described in the description of the preferred embodiment to follow. The scope of this invention will be determined by the claims.

BRIEF DESCRIPTION OF THE DRAWINGS

FIG. 3 is a sectional view taken along line 3—3 of FIG. 2 of the attachment mechanism for attaching the recapping system of this invention to a pole;

FIG. 4 is a sectional view taken along line 4—4 of FIG. 2 illustrating the gripping mechanism holding the syringe with needle cap in its proper position;

FIG. 5 is a side view illustrating the removal and reinsertion of a needle with syringe into a needle cap being held by the gripping mechanism of this invention; and FIG. 6 is a schematic view of a typical operating room layout illustrating the utilization of the recapping system of this invention by an anesthesiologist or nurse anesthetist.

DESCRIPTION OF THE PREFERRED EMBODIMENT

Figure 1:
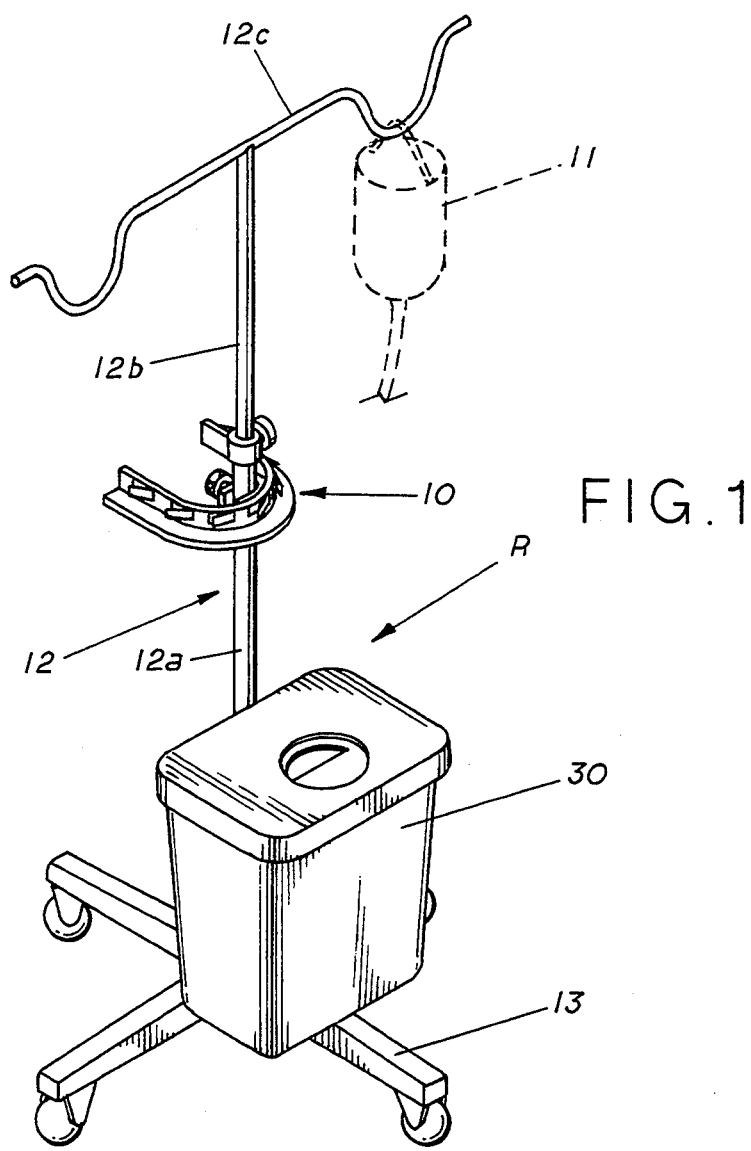
FIG. 1 is a perspective view of the recapping system of this invention mounted onto an IV pole in combination with a container for receiving sharp instruments for later, safe disposal.

Referring to the drawings, the letter R generally designates the syringe with needle recapping system of the preferred embodiment of this invention mounted onto an intravenous feeding pole commonly known as an "IV" pole 12. The recapping system includes the apparatus generally designated as 10 for one-handed removal of a syringe S with needle N from a gripped needle cap C and subsequent replacement of the syringe with needle into the gripped needle cap.

The IV pole 12 illustrated in FIG. 1 may be one of any suitable design for such a device for holding intravenous feeding bottles such as 11. Such an IV pole 12 includes lower base pole portion 12a which is attached to any type of suitable rolling support such as the 4-wheeled rolling support base designated as 13 in FIG. 1. The IV pole further includes an upper telescoping pole portion 12b which terminates in a laterally extending IV support 12c.

Figure 2:
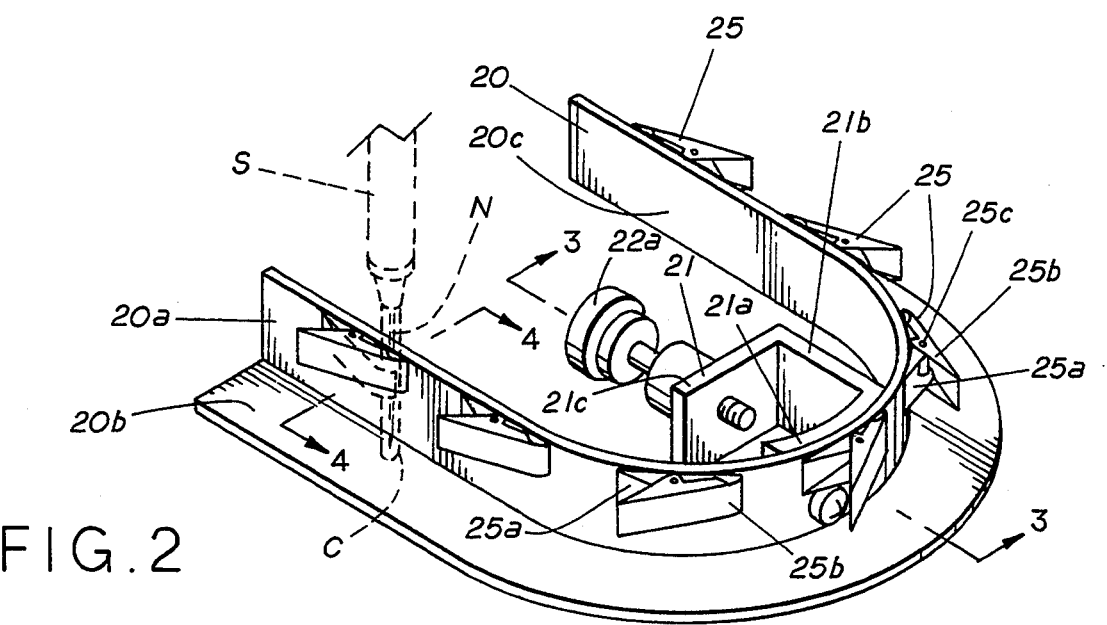
FIG. 2 is a perspective view of the recapping system of this invention removed from the IV pole and illustrating a syringe with needle and cap in a gripped position.

The apparatus 10 for recapping, as illustrated in perspective in FIGS. 1 and 2, includes a frame 20 which is generally U-shaped as viewed from above. It should be understood that the frame 20 may be any other suitable shape including a straight frame member or a frame member in any other curved configuration. The frame member 20 is L-shaped as viewed in the cross-section of FIGS. 3 and 4 and includes a vertical section 20a and a horizontal section 20b.

An attachment mechanism 21 is attached to the rear surface 20c of the frame member for mounting the frame member 20 onto the IV pole at any suitable height. The attachment member 21 is generally U-shaped as viewed from the top as shown in FIG. 2 and includes an internal curved segment 21a integrally formed with a lateral segment 21b and a third, outer segment 21c. The outer segment 21c includes a threaded mounting screw 22 terminating in a knob 22a so that the attaching member 21 can mount the apparatus frame 20 at any height along the telescoping pole portions 12a and 12b of the IV pole 12.

The recapping apparatus 10 further includes a plurality of spaced needle cap gripping mechanisms 25 which are suitably spaced with respect to each other along the vertical frame segment 20a. Each gripping mechanism 25 is identical and thus only one will be described. Each gripping mechanism 25 includes a first gripping member or gripping jaw 25a which is attached to the vertical surface of the vertical frame segment 25a by any suitable means such as a screw (not shown). The gripping mechanism further includes a second gripping element or jaw 25b which is attached to the first gripping element by a suitable pin 25c so that the two gripping elements are mounted for pivotal movement with respect to each other. A spring is mounted about the connecting pin 25c and is positioned to engage both gripping elements 25a and 25b in order to resiliently urge the gripping surfaces toward each other. In this manner, a needle cap C may be resiliently held in a standup, vertical position as shown in FIGS. 2, 3 and 4. The height h of the vertical frame segment 20a is such that with the gripping element 25 mounted thereon, the needle cap C may be landed against the surface of the bottom transverse frame member 20b with the open end of the needle cap C exposed for insertion of the needle N with syringe S into the needle cap C.

Referring again to FIG. 1, a container 30 is also mounted onto the IV pole for purposes of receiving sharp objects for ultimate disposal. Such a container is sometimes called a "sharps" container and may be one of several varieties currently manufactured. One such container is manufactured by Sage Products, Inc. and is stated to be covered by one or more U.S. Pat. Nos. 4,375,849; 4,657,139; 4,779,728; Re. 33,413; 4,863,057 and 292,037. The sharps container 30 may be mounted onto the IV pole base section 12a by any suitable means such as an attachment mechanism of the same type as utilized for the needle recapping apparatus 10 of this invention. In this manner, after a syringe S with needle has been used and is no longer needed, the medical professional may dispose of the needle with syringe by dropping it into the sharps container 30.

Referring now to FIG. 6, a schematic for a typical operating room is illustrated. The patient's bed or operating table 40 includes outwardly extending "boards" 41 and 42 which receive the arms of the patient P. An anesthesiologist or nurse anesthetist sits in the chair 43. To the left of the anesthetist is the drug cart 44 and to the right of the anesthetist is the gas machine 45, all of which is well-known in the art. The IV pole 12 may also be placed to the left of the anesthetist with the recapping apparatus 10 mounted thereon and within easy reach of the anesthetist. During an operation, the anesthetist may utilize some to all of the gripping mechanisms 25 of the recapping apparatus. Syringes with needles may be mounted in one or more of the gripping mechanisms 25 so that syringes S with needles N are ready to use or may be replaced into caps C for safe, temporary storage until reuse. At the end of the operation, all of the syringes S with needles are dropped into the sharps container 30. In this manner, the recapping apparatus T keeps all of the syringes with needles in easy reach but allows them to be stored in a capped position between uses.

Having described the invention above, various modifications of the techniques, procedures, material and equipment will be apparent to those in the art. It is intended that all such variations within the scope and spirit of the appended claims be embraced thereby.

For example, there are many environments which the needle recapping system of this invention can be used such as during surgery as previously discussed but also in patient holding areas, recovery rooms, intensive care areas, surgical pharmacies, outpatient service areas, therapeutic clinics, emergency rooms, emergency vehicles, various laboratories and anywhere else where needles with syringes are used.

I claim:

1. Apparatus providing for one-handed removal of a syringe with needle from a needle cap and subsequent replacement, comprising:

a frame having means for attachment to a stationary object;

a gripping mechanism attached to said frame, said gripping mechanism including resiliently urged, internal gripping surfaces to receive and hold a syringe with needle having a needle cap thereon, said syringe with needle being removable from said needle cap and replaceable into said needle cap which is held in a gripped position by said gripping mechanism; and said frame includes first and second surfaces forming a generally L-shaped portion when viewed in cross-section wherein said friction-gripping mechanism is attached to said first surface a sufficient distance away from said second surface such that the closed end of a needle cap gripped in said gripping mechanism will be landed onto said second surface to cooperate with said gripping mechanism to hold said needle cap stationary during replacement of a syringe with needle into a needle cap.

2. The structure set forth in claim 1, including:

said gripping mechanism including a first gripping member attached to said frame and a second gripping member mounted for pivotal movement with respect to said first gripping member; and a resilient element engaging said first and second gripping members to urge gripping portions of said members toward each other to resiliently grip said needle cap.

3. Apparatus for the safe removal of a syringe with needle from a needle cap and subsequent replacement thereof, comprising:

a generally U-shaped frame having an attachment element for attaching said U-shaped frame to a stationary object;

a plurality of friction gripping mechanisms attached to said frame, said gripping mechanism including resiliently urged, internal gripping surfaces to receive and hold the needle cap of a syringe with needle having a needle cap thereon, said syringe with needle being removable from said needle cap and replaceable into said needle cap which is held in a gripped position by said gripping mechanism and said generally U-shaped frame includes first and second surfaces forming a generally L-shaped portion when viewed in cross-section wherein said friction gripping mechanism is attached to said first surface a sufficient distance away from said second surface such that the closed end of a needle cap gripped in said gripping mechanism will be landed onto said second surface to cooperate with said gripping mechanism to hold said needle caps stationary during replacement of a syringe with needle into a needle cap.

4. The structure set forth in claim 3, including:

each of said friction gripping mechanisms including a first gripping member attached to said frame and a second gripping member mounted for pivotal movement with respect to said first gripping member;

a resilient element engaging said first and second gripping members to urge said gripping members toward each other to resiliently grip said needle cap.

5. The structure set forth in claim 1, including:
said stationary object in an intravenous feeding pole.

6. The structure set forth in claim 3, including:
said stationary object in an intravenous feeding pole.

7. The structure set forth in claim 5, further including:
a sharps container for receiving used needles and a mounting mechanism for attachment of said sharps container to said pole below said U-shaped frame.

8. The structure set forth in claim 3, including:
said friction gripping mechanisms being mounted to said U-shaped frame at spaced intervals to allow the user to remove and replace a syringe from one friction gripping mechanism without touching a syringe with needle and cap held in an adjacent gripping mechanism.

* * * * *